US008386190B2

(12) United States Patent
Li

(10) Patent No.: US 8,386,190 B2
(45) Date of Patent: Feb. 26, 2013

(54) SYSTEM AND METHOD FOR IDENTIFYING NETWORKS OF TERNARY RELATIONSHIPS IN COMPLEX DATA SYSTEMS

(75) Inventor: Ker-Chau Li, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 13/280,167

(22) Filed: Oct. 24, 2011

(65) Prior Publication Data

US 2012/0102068 A1 Apr. 26, 2012

Related U.S. Application Data

(62) Division of application No. 12/168,257, filed on Jul. 7, 2008, now Pat. No. 8,046,174, which is a division of application No. 10/330,007, filed on Dec. 24, 2002, now Pat. No. 7,406,384.

(60) Provisional application No. 60/343,990, filed on Dec. 26, 2001.

(51) Int. Cl.
*G06F 19/00* (2011.01)
*C12Q 1/68* (2006.01)

(52) U.S. Cl. .......................... 702/19; 435/6.1
(58) Field of Classification Search ..................... None
See application file for complete search history.

(56) References Cited

U.S. PATENT DOCUMENTS 6,420,105 B1 7/2002 Landfield et al.
6,421,668 B1 7/2002 Yakhini et al.

OTHER PUBLICATIONS

Spellman et al.; "Comprehensive Identification of Cell Cycle-regulated Genes of the Yeast *Saccharomyces cerevisiae* by Microarray Hybridization," Molecular Biology of the Cell, vol. 9, pp. 3273-3297; Dec. 1998.
Bhattacharjee et al.; "Classification of Human Lung Carcinomas by mRNA Expression Profiling Reveals Distinct Adenocarcinoma Subclasses," Proceedings of the National Academy of Sciences USA, vol. 98, Nov. 20, 2001, pp. 13790-13795.
Tamayo et al.; Proceedings of the National Academy of Sciences USA, vol. 96, Mar. 1999, pp. 2907-2912.
Marcotte et al.; "A Combined Algorithm for Genome-Wide Prediction of Protein Function," Nature, vol. 402, Nov. 4, 1999, pp. 83-86.
Kulkarni et al,; "Gln3p Nuclear Localization and Interaction with Ure2p in *Saccharomyces cerevisiae*," Journal of Biological Chemistry, vol. 276, No. 34, Aug. 24, 2001, pp. 32136-32144.
Crauwels et al.; "The Sch9 Protein Kinase in the Yeast *Saccharomyces cerevisiae* Controls cAPK Activity and Is Required for Nitrogen Activation of the Fermentable-Growth-Medium-Induced (FGM) Pathway," Microbiology, vol. 143, 1997, pp. 2627-2637.
Saraste, M.; "Oxidative Phosphorylation at the fin de siecle," Science, vol. 283, Mar. 5, 1999, pp. 1488-1493.
Alon et al.; "Broad Patterns of Gene Expression Revealed by Clustering Analysis of Tumor and Normal Color Tissues Probed by Oligonucleotide Arrays," Proceedings of the National Academy of Sciences USA, vol. 96, Jun. 1999, pp. 6745-6750.
Giordano et al; "Organ-Specific Molecular Classification of Primary Lung, Colon, and Ovarian Adenocarcinomas Using Gene Expression Profiles," American Journal of Pathology, vol. 159, No. 4. Oct. 2001. pp. 1231-1238.
Alter et al; "Singular Value Decomposition for Genome-Wide Expreession Data Processing and Modeling," Proceedings of the National Academy of Sciences USA, vol. 97, No. 18, Aug. 29, 2000, pp. 10101-10106.
Abadjieva et al; "A New Yeast Metabolon Involving at Least the Two First Enzymes of Arginine Biosynthesis," Journal of Biological Chemistry, vol. 276, No. 46, Nov. 16, 2001, pp. 42869-42880.
Finch, C.E.; Ruvkun, G.; "The Genetics of Aging," Annual Review of Genomics and Human Genetics 2001, vol. 2, pp. 435-462.
Cyert, M.S.; "Genetic Analysis of Calmodulin and Its Targets in *Saccharomyces cerevisiae*," Annual Review of Genetics 2001, vol. 35, pp. 647-672.
Russnak et al.; "A Family of Yeast Proteins Mediating Bidirectional Vacuolar Amino Acid Transport," Journal of Biological Chemistry, vol. 276, No. 26, Jun. 29, 2001, pp. 23849-23857.
Scherf et al.; "A Gene Expression Database for the Molecular Pharmacology of Cancer," Nature Genetics, vol. 24, Mar. 2000, pp. 236-244.
Eisen et al.; "Cluster Analysis ad Display of Genone-Wide Expression Patterns," Proceedins of the National Academy of Sciences USA, vol. 95, Dec. 1998, pp. 14863-14868.
Brown et al.; "Knowledge-Based Analysis of Microarray Gene Expression Data by Using Support Vector Machines," Proceedings of the National Academy of Sciences USA, vol. 97, No. 1, pp. 262-267.
Smart et al.; "Combinatorial Regulation of the *Saccharomyces cerevisiae* CAR1 (Arginiase) Promoter in Response to Multiple Environmental Signals," Molecular and Cellular Biology, Oct. 1996, pp. 5876-5887.
Fabrizio et al.; "Regulation of Longevity and Stress Resistance by Sch9 in Yeast," Science, vol. 292, Apr. 13, 2001, pp. 288-290.
Lin et al.; "Requirement of NAD and SIR2 for Life-Span Extension by Calorie Restriction in *Saccharomyces cerevisiae*," Science, vol. 289, Sep. 22, 2000, pp. 2126-2128.
Furuchi et al.; "Two Nuclear Proteins, Cin5 and Ydr259c, Confer Resistance to Cisplatin in *Saccharomyces cerevislae*," Molecular Pharmacology, vol. 59, No. 3, 2001, pp. 470-474.
Wingender et al.; "Transfac: An Integrated System for Gene Expression Regulation," Nucleic Acids Research 2000, vol. 28, No. 1, pp. 316-319.
Estruch, F.; "Stress-Controlled Transcription Factors, Stress-Induced Genes and Stress Tolerance in Budding Yeast," FEMS Microbiology Reviews, vol. 24, 2000, pp. 469-486.
Brown, P.O.; Botstein, D.; "Exploring the New World of the Genome with DNA Microarrays," Nature Genetics Supplement, vol. 21, Jan. 1999, pp. 33-37.

(Continued)

*Primary Examiner* — John S Brusca
(74) *Attorney, Agent, or Firm* — John P. O'Banion

(57) ABSTRACT

A system and method for identifying high order associations between variables in complex systems that is particularly useful where there is no correlation or weak correlation between variables due to the influence of a third variable, a ternary relationship. The ternary relationship describes how the variation in the pattern of association between a pair of variables, including its sign and strength, is mediated by a third variable. In one embodiment applied to gene expression data, the activity of pairs of correlated genes due to the activity of one or more third genes is shown.

8 Claims, 5 Drawing Sheets

OTHER PUBLICATIONS

Sillje et al.; "Function of Trehalose and Glycogen in Cell Cycle Progression and Cell Viability in *Sachharomyces cerevisiae*," Journal of Bacteriology, vol. 181, No. 2, Jan. 1999, pp. 396-400.

Forgac, M.; "Structure and Properties of the Vacuolar (H+)-ATPases," The Journal of Biological Chemistry, vol. 274, No. 19, May 7, 1999, pp. 12951-12954.

Cohen et al.; "A Novel Family of Yeast Chaperons Involved in the Distribution of V-ATPase and Other Membrane Proteins," Journal of Biological Chemistry, vol. 274, No. 38, Sep. 17, 1999. pp. 26885-26893.

Peters, J.-M.; "Subunits and Substrates of the Anaphase-Promoting Complex," Experimental Cell Research, vol. 248, 1999, pp. 339-349.

De La Cruz et al.; "Unwinding RNA in *Saccharomyces cerecisiae*: DEAD-box Proteins and Related Families," Trends in Biochemical Sciences, May 1999, pp. 192-198.

Karlin, S.; Mrazek,J.; "Predicted Highly Expressed Genes of Diverse Prokaryotic Genomes," Journal of Bacteriology, vol. 182, No. 18, Sep. 2000, pp. 5238-5250.

Strauss, E.; "Longevity: Growing Old Together," Science, vol. 292, Apr. 6, 2001, pp. 41-43.

Luikenhuis et al.; "The Yeast *Saccharomyces cerevisiae* Contains Two Glutaredoxin Genes That Are Required for Protection Against Reactive Oxygen Species," Molecular Biology of the Cell, vol. 9. May 1998, pp. 1081-1091.

Lockhart, D.J.; Winzeler, E.A.; "Genomics, Gene Expression and DNA Arrays," Nature, vol. 405, Jun. 15, 2000, pp. 827-836.

Amitrano et al.; "GAP1 Activity of Dependent oncAMP in *Saccharomyces cerevisiae*," FEMS Microbiology Letters, vol. 151, 1997, 99. 131-133.

ter Schure, E.G.; "The Role of Ammonia Metabolism in Nitrogen Catabolite Repression in *Saccharomyces cerevlsiae*," FEMS Microbiology Reviews, vol. 24, 2000, pp. 67-83.

Dohn et al.; "Receptor Tyrosine Kinase Eph2 is Regulated by p53-Family Proteins and Induces Apoptosis," Oncogene, vol. 20, 2001, pp. 6503-6515.

Taylor et al.; "Regulation of P311 Expression by Met-Hepatocyte Growth Factor/Scatter Factor and the Ubiquitin/Proteasome System," Journal of Biological Chemistry, vol. 275, No. 6, Feb. 11, 2000. pp. 4215-4219.

Mariani et al.; "identification and Validation of P311 as a Glioblastoma Invasion Gene Using Laser Capture Microdissection," Cancer Research, vol. 61, May 15, 2001, pp. 4190-4196.

Ghosh et al.; "A Novel 16-Kilodalton Cellular Protein Physically Interacts with and Antagonizes the Functional Activity of c-myc Promoter-Binding Protein 1," Molecular and Cellular Biology, vol. 21. No. 2. Jan. 2001, pp. 655-662.

Yoshida et al.; "Metastasis-Suppressor Genes: A Review and Perspective on an Emerging Field," Journal of the National Cancer Institute, vol. 92, No. 21, Nov. 21, 2000, pp. 1717-1730.

Chow et al.; "The Role of nm23-H1 in the Progression of Transitional Cell Bladder Cancer," Clinical Cancer Research, vol. 6, Sep. 2000, pp. 3595-3599.

Benson et al.; "Expression of MX11, a Myc Antagonist, Is Regulated by Sp1 and AP2," Jounal of Biological Chemistry, vol. 274, No. 40, Oct. 1, 1999, pp. 28794-28802.

Parrou et al.; "STRE- and cAMP-independent Transcriptional Induction of *Saccharomyces cerevisiae* GSY2 Encoding Glycogen Synthase during Diauxic Growth on Glucose," Yeast, vol. 15, 1999, pp. 1471-1484.

DeRisi et al.; "Exploring the Metabolic and Genetic Control of Gene Expression on a Genomic Scale," Science, vol. 278, Oct. 24, 1997, pp. 680-686.

Ito et al.; "A Comprehensive Two-Hybrid Analysis to xplore the Yeast Protein Interactome," Proceedings of the National Academy of Sciences USA, vol. 98, No. 8, Apr. 10, 2001, pp. 4569-4574.

Tye, B.K.; "MCM Proteins in DNA Replication," Annual Review of Biochemistry 1999, vol. 68, pp. 649-686.

Colantuoni et al.; "Applications Note: SNOMAD: (Standardization and NOrmalization of MicroArray Data): Web-Accessible Gene Expression Data Analysis," Bioinformatics, vol. 18, No. 11, 2002, pp. 1540-1541.

Yu et al.; "Overexpression of ErbB2 Blocks Taxol-Induced Apoptosis by Upregulation of p21(Cip1), which inhibits p34(Cdc2) Kinase," Molecular Cell, vol. 2, Nov. 1998, pp. 581-591.

Li, Ker-Chau et al.; "The Data-Smoothing Aspect of Stein Estimates," The Annals of Statistics, vol. 12, No. 3, pp. 887-897, (1984).

Li, Ker-Chau; "From Stein's Unbiased Risk Estimates to the Method of Generalized Cross Validation," The Annals of Statistics, vol. 13, No. 4, pp. 1352-1377, (1985).

Li, Ker-Chau et al.; "A Simple Statistical Model for Depicting the CDC15-Synchronized Yeast Cell-Cycle Regulated Gene Expression Data," Statistica Sinica, vol. 12, No. 1, pp. 141-158, Jan. 2002.

Li, Ker-Chau et al.; "Sliced Inverse Regression for Dimension Reduction," Journal of the American Statistical Association, vol. 86, No. 414, pp. 316-342, Jun. 1991.

Li, Ker-Chau et al.; "Dimension Reduction for Multivariate Response Data," Work in Progress, pp. 1 thru 26 with 11 pages of figures, Feb. 5, 2002.

Li, Ker-Chau et al.; "A Bayesian Insertion/Deletion Robust Algorithm for Distant Protein MOTIF Searching Via Entropy Filtering," Work in Progess, pp. 1 thru 38, Sep. 27, 2000.

Li, Ker-Chau; "On Principal Hessian Directions for Data Visualization and Dimension Reduction: Another Application of Stein's Lemma," Journal of the American Statistical Association, vol. 87, No. 420, pp. 1025-1039, Dec. 1992.

Babler, Jochen et al.; "Identification of a 60S Preribosomal Particle That Is Closely Linked to Nuclear Export," Molecular Cell, vol. 8, pp. 517-529, Sep. 2001.

Shore, Paul et al.; "The MADS-Box Family of Transcription Factors," Journal of Biochemistry, vol. 229, pp. 1-13, (1995).

Grotzinger, C. et al.; "Li-Cadherin: A Marker of Gastric Metaplasia and Neoplasia," Gut Journal, vol. 49, pp. 73-81, (2001).

Myeroff, Lois L. et al.; Increased NM23-H1 and NM23-H2 Messenger RNA Expression and Absence of Mutations in Colon Carcinomas of Low and High Metastatic Potential, Journal of the National Cancer Institute, vol. 85, No. 2, pp. 147-152, Jan. 20, 1993.

DuBois, E. et al.; "Integration of the Multiple Controls Regulating the Expression of the Arginase Gene Car1 of *Saccharomyces cerevisiae* in Response to Different Nitrogen Signals: Role of Gln3p, ArgRp-Mcm1p, and Ume6p," Mol. Gen. Genet, vol. 253, pp. 568-580, (1997).

Martinez, J.A. et al.; "Overexpression of nm23-H1 and nm23-H2 Genes in Colorectal Carcinomas and Loss of nm23-H1 Expression in Advanced Tumour Stages," Gut Journal, vol. 37, pp. 712-720, (1995).

Carter, A.T. et al.; "PRS1 is a Key Member of the Gene Family Encoding Phosphoribosylpyrophosphate Synthetase in *Saacharomyces cerevisiae*," Mol. Gen. Genet. vol. 254, pp. 148-156, (1997).

Weaver, Robert; "Molecular Biology-Second Edition," Cover page, Title page, pp. 406-407, McGraw-Hill Companies, (2002).

Alberts, Bruce et al.; "Molecular Biology of the Cell-Third Edition," Cover page, Title page, pp. 47, Garland Publishing, (1994).

Voet, Donald et al.; "Biochemistry-Second Edition," Cover page, Title page, pp. 472, John Wiley & Sons, (1995).

Lodisb, Harvey et al.; "Molecular Cell Biology-Third Edition," Cover page, Title page, pp. 771, Scientific American Books, (1995).

Cook, R. Dennis et al.; "Reweighting to Achieve Elliptically Contoured Covariates in Regression," Journal of the American Statistical Association, vol. 89, No. 426, pp. 592-599, (1994).

Cook, R. Dennis; "Regression Graphics," Cover page, Title page, pp. 224-228, John Wiley & Sons, (1998).

Molenaar, I.W. et al. (ads.); "Encyclopedia of Statistical Sciences-vol. 6," Multivariate Analysis to Plackett and Burman Designs, Cover page, Title page, pp. 347-367, (1982).

Molenaar, 1.W. et al. (eds.); "Encyclopedia of Statistical Sciences-vol. 2," Classification to Eye Estimate, Cover page, Title page, pp. 193-204, (1982).

Morrison, Donald F.; "Multivariate Statistical Methods-Third Edition," Cover page, Title page, pp. 90-94, (1990).

Li, Ker-Chau; "Genome-Wide Coexpression Dynamics: Theory and Application," PNAS, vol. 99, No. 26, pp. 16875-16880, Dec. 24, 2002.

Clancy, David J. et al.; "Extension of Life-Span by Loss of Chico, a *Drosophila* Insulin Receptor Substrate Protein," Science, vol. 292, pp. 104-106, Apr. 6, 2001.

Bijiani, Rahul et al.; "Prediction of Biologicall Significant Components From Microarray Data: Independently Consistent Expression Discriminator(ICED)," Bioinformatics, vol. 19, No. 1, pp. 62-70, (2003).

Staunton, Jane E. et al.; "Chemosensitivity Prediction by Transcriptional Profiling," PNAS, vol. 98, No. 19, pp. 10787-10792, Sep. 11, 2001.

Orr, M.S. et al.; "Large-Scale Gene Expression Analysis in Molecular Target Discovery," Leukemia, vol. 16, pp. 473-477, (2002).

Ashburner, Michael et al.; "Gene Ontology: Tool for the Unification of Biology," Nature Genetics, vol. 25, pp. 25-29, May 2000.

Golub, T.R. et al.; "Molecular Classification of Cancer: Class Discovery and Class Prediction by Gene Expression Monitoring," Science, vol. 286, p. 531-537, Oct. 15, 1999.

Hazbun, Tony R. et al.; "Networking Proteins in Yeast," PNAS, vol. 98, No. 8, pp. 4277-4278, Apr. 10, 2001.

Holter, Neal S. et al.; "Fundamental Patterns Underlying Gene Expression Profiles: Simplicity From Complexity," PNAS, vol. 97, No. 15, pp. 8409-8414, Jul. 19, 2000.

Jiang, Cecilia H. et al.; "The Effects of Aging on Gene Expression in the Hypothalamus and Cortex of Mice," PNAS, vol. 98, No. 4, pp. 1930-1934, Feb. 13, 2001.

Lee, Cheol-Koo et al.; "Gene Expression Profile of Aging and its Retardation by Caloric Restriction," Science, vol. 285, pp. 1390-1393, Aug. 27, 1999.

Quackenbush, John; "Microarray Data Normalization and Transformation," Nature Genetics Supplement, vol. 32, pp. 496-501, Dec. 2002.

Banerjee, Debabrata et al.; "Novel Aspects of Resistance to Drugs Targeted to Dihydrofolate Reductase and Thymidylate Synthase," Biochimica et Biophysica Acts, vol. 1587, pp. 164-173, (2002).

Gailus-Durner, Valerie et al.; "Experimental Data of a Single Promoter Can be Used for in Silico Detetion of Genes With Related Regulation in the Absence of Sequence Similarity," Mammalian Genome, vol. 12, pp. 67-72, (2001).

Ross, Douglas T. et al.; "Systemactic Variation in Gene Expression Patterns in Human Cancer Cell Lines," Nature Genetics, vol. 24, pp. 227-235, Mar. 2000.

Zhou, Xianghong et al.; "Transitive Functional Annotation by Shortest-Path Analysis of Gene Expression Data," PNAS, vol. 99, No. 20, pp. 12783-12788, Oct. 1, 2002.

Tatar, M. et al.; "A Mutant *Drosophila* Insulin Receptor Homolog That Extends Life-Span and Impairs Neuroendocrine Function," Science, vol. 292, pp. 107-110, Apr. 6, 2001.

Wyrick, John J. et al.; "Deciphering Gene Expression Regulatory Networks," Current Opinion in Genetics & Development, vol. 12, pp. 130-136, (2002).

Zhang, Michael Q.; "Extracting Functional Information From Microarrays: A Challenge for Functional Genomics," PNAS, vol. 99, No. 20, pp. 12509-12511, Oct. 1, 2002.

Proc. Natl. Acad. Sci. Online Publicatino Notice, retrieved from <http://www.pnas.org/cgi/content/full/99/26/16875?ijkey=82b374df17d4c59a4a815d29d49dc00a7b9a94e0 on Jun. 8, 2006.

Qian et al. Journal of Molecular Biology, vol. 314, pp. 1053-1066 (2001).

YM Seminar Announcement, printed on Sep. 14, 2005 from the internet <http://biinfo.ym.edu.tw/edu/seminars/seminar92_2.htm>.

NUK Talk, a seminar announcement, printed on Sep. 13, 2005 from the internet <http://stat.nuk.edu.tw/talk?92-2.htm>.

Merriam-Webster Online, definition for "stagger", <http://www.m-w.com/cgi-bin/dictionary?book=Dictionary&va=stagger>.

United States Patent & Trademark Office (USPTO), International Search Report issued on May 21, 2003, including claims searched, related PCT International Application No. PCT/US02/41184, pp. 1-9.

SYSTEM AND METHOD FOR IDENTIFYING NETWORKS OF TERNARY RELATIONSHIPS IN COMPLEX DATA SYSTEMS

CROSS-REFERENCE TO RELATED APPLICATIONS

This application is a division of U.S. patent application Ser. No. 12/168,257 filed on Jul. 7, 2008, now U.S. Pat. No. 8,046,174 incorporated herein by reference in its entirety, which is a division of U.S. patent application Ser. No. 10/330, 007 filed on Dec. 24, 2002, now U.S. Pat. No. 7,406,384 incorporated herein by reference in its entirety, which claims priority from U.S. provisional application Ser. No. 60/343, 990 filed on Dec. 26, 2001, incorporated herein by reference in its entirety.

This application is also related to PCT International Publication No. WO/2003/058503, published on Jul. 17, 2003, incorporated herein by reference in its entirety.

STATEMENT REGARDING FEDERALLY SPONSORED RESEARCH OR DEVELOPMENT

This invention was made with Government support under Grant No. DMS-9803459, Grant No. 0104038, and Grant No. 0201005, awarded by the National Science Foundation. The Government has certain rights in this invention

INCORPORATION-BY-REFERENCE OF MATERIAL SUBMITTED ON A COMPACT DISC

Not Applicable

BACKGROUND OF THE INVENTION

1. Field of the Invention

This invention pertains generally to large database analysis, and more particularly to a system and method for identifying global association patterns in databases to facilitate an understanding of complex systems with numerous variables such as biological systems.

2. Description of Related Art

The development of computer systems with high-density memory devices and efficient communications, have lead to the appearance of large databases with complex data structures. For example, point of sale information from retailers, financial and insurance transactions and claims, credit card activity and similar information from across the country is stored in a number of large databases. Extracting useful information from substantially large databases to develop business or sales strategies is problematic. Various methods of "data mining" have been developed to identify and interpret patterns and global relationships in such databases so that information can be derived about the individual variables and allow strategic decision making and reliable predictions. Data mining allows the observance of trends, rules, patterns, constraints, irregularities and correlations and the like from large volumes of collected data. The process of data mining may use such methods as clustering, decision trees, association rule generation, memory based reasoning and neuro-analysis. The most suitable analysis will depend on the nature of the collected data to be analyzed and purpose of the analysis.

Databases relating to the research of biological systems tend to be particularly large and complex. Cellular activities form a complex biological system including a network of often interrelated subsystems. The rules for governing the genetic circuitry of expressing some genes and repressing others, in response to a variety of both inner and outer stimuli, are largely unknown. Modern DNA gene arrays allow the simultaneous measurement of the levels of expression of thousands of genes from a single biological sample. The gene or micro array is a high throughput biochemistry technique for generating data about the quantity of mRNA expressed by each gene in cells of an organism under a set of conditions. Here "conditions" broadly refers, for example, to doses of a tumor growth inhibition agent, times in a cell cycle, strains of mutation, types of cancer, and so on. The data, commonly referred to as a gene expression profile, can be used to infer the global cellular activities that would be hard to describe otherwise.

However, the statistical analysis of gene array data in molecular biology is usually the greatest difficulty faced with the use of the technique. Large volumes of array data typically overwhelm traditional methods and models of data analysis. The ultimate use of this powerful biotechnology hinges on how to process the data.

One procedure for distilling information from microarray data is through the use of correlation. Correlation is a traditional way of summarizing the relationship between any two variables in a system after the collection of empirical data. A positive correlation between variables implies similar behavior and a similar role within the system while a negative correlation indicates the opposite behavior and complementary role.

It is well-accepted that genes with similar profiles are likely to share common cellular roles and participate in related pathways. Pearson's correlation coefficient, (a popular measure of similarity), is thought to conform well to the intuitive biological notion of what it means for two genes to be "coexpressed". For any pair of genes (X, Y), a correlation can be computed using formulas in the prior art. Then all correlations are compared with each other or with a default value to determine the statistical significance. High and significant correlation is interpreted as a likely evidence for functional association between genes, meaning that their gene products are more likely to form a protein complex or participate in common metabolic or regulatory pathways and biological processes. This correlation-based similarity analysis together with variations and extensions for clustering or classification has generated enormous biologically significant results. Indeed, many gene clusters with similar expression patterns and shared roles in common cellular processes have been observed, including histones, cytoplasmic ribosomal proteins, proteasome, cytochrome-C, ATPase complex, and others.

Positively or negatively associated variables, once detected, can be used as building blocks toward the understanding of the system and for predicting the behavior of the system. But in the extremely complex systems, the vast majority of cases turn out producing no or weak correlations between variables. This often is the rule, even for those variables that are suspected to be closely related in theory. This renders the traditional correlation-based similarity analysis useless.

Despite the many successful applications, the use of Pearson's correlation coefficient, including the related Spearman's rho and Kendall's tau known in the art, are not flexible enough to describe all of the kinds of in vivo association patterns between genes. There are numerous cases of failure with conventional correlation analysis where functional association is evident according to experimental evidence, yet the statistical correlation from gene assay evidence is practically zero. The abundance of such negative results constitutes a bottleneck in distilling more information from microarray data.

The observed lack of correlation can be due to the noises in the data. But quite often the primary reason is due to the biological complexity of the subsystem and nature of its components such as the pleiotropic or multiple functions of a protein, varying cellular oxidization-reduction states, fluctuating hormone levels or other cellular signals, and the like. The case of two transcription factors, Max and thyroid hormone receptor (TR) are illustrative. These factors can serve either as activators or as repressors, depending on the other molecules that are bound to them. Max can bind to Myc and form a Myc-Max dimer that acts as a transcription activator. But when bound to Mad, the Mad-Max dimer serves as a repressor. For the case of TR, it associates with RXR to form a TR-RXR dimer that serves as a repressor in the absence of thyroid hormone. In the presence of thyroid hormone, the TR-RXR dimer is converted into an activator. Histone deacetylation is involved in both repressing events. Thus for example, if X is taken to be the expression profile of the gene encoding TR and Y is taken to be the profile of one of its target genes, then X and Y may be either positively correlated or negatively correlated, depending on the hormone level. If the hormone level fluctuates in an unspecific manner, the opposing directions of correlation may cancel out each other and no similarity based analysis may succeed in detecting the functional association between X and Y. Thus, uncovering the biological reasons behind the lack of detectable correlation is a new approach for understanding the gene expression network.

Accordingly, there is a need for a system and method that aims at the identification of an advanced type of association between variables in complex systems where the correlation between variables is not readily apparent but is in fact existent and is constantly changing in response to the change of a state variable from unknown sources. The present system simultaneously identifies such variables and points to variables that are correlated with the state variable. The present invention generally overcomes the deficiencies found in existing equipment, systems and methods that fail to exploit structures that are not correlated or are weakly correlated.

BRIEF SUMMARY OF THE INVENTION

The present invention generally comprises a system and method for identifying a network of novel ternary relationships between variables in a complex data system. The ternary relationship describes how the variation in the pattern of association between a pair of variables, including its sign and strength, is mediated by a third variable from the background.

By way of example, and not of limitation, the system for describing high order associations between variables can be illustrated through the use of gene expression profiles. Modern DNA gene arrays allow the simultaneous measurement of the levels of expression of thousands of genes from a single biological sample. Gene arrays are described as either macroarrays, containing sample spot sizes of 300 microns or larger and microarrays with sample spot sizes of 200 microns or less in diameter. DNA microarrays typically comprise a cDNA probe from 500 to 5000 bases in length or an oligonucleotide or peptide nucleic acid probe that is adhered to a glass or nylon surface. When exposed to the sample, the probes bind complimentary mRNA present in the sample indicating the corresponding gene is turned on.

Comparisons of microarray data from samples in two different biological conditions allow the detection of the presence of differential gene expression. Such comparisons allow one to determine if there is a statistically significant change in gene expression between a first condition and a second condition such as with a tumor and a normal cell or cells in the presence or absence of a drug.

To distill any information from gene expression data, it often requires sophisticated statistical reasoning and computer skills because of the volume of data that is produced. Underlying many powerful methods including those from clustering, classification and dimension reduction is the similarity between gene profiles measured by Pearson's correlation coefficient or the related statistics. However, in biological systems whether two genes are co-expressed is affected by activities of other genes and sometimes a positive correlation can even be turned into a negative one. Accordingly, the correlated expression patterns of a pair of genes may not be apparent from traditional correlation analysis. In fact, many genes associated with the same pathway are not correlated or are weakly correlated. There are several situations where functional association does not lead to co-regulated gene expression. Often the correlation between the expression of the regulator and the gene it regulates is approximately zero. The same is often true for transcription factors and their target genes; enzymes in the same or crossed pathways and subunits in protein complexes.

The term liquid association (LA), "liquid" as opposed to "steady", is used to conceptualize the internal evolution of co-expression patterns for a pair of genes (X,Y) in response to constant changes in the cellular state variables. Because the relevant cellular states are typically unknown, it is difficult to detect this novel type of association from the profiles of X and Y alone. However, if the state change turns out to be associated with the differential expression of a third gene Z, then the profile of Z can be utilized to screen the scatterplot of (X,Y) for the intrinsic expression patterns termed LA activity. This creates a ternary relationship between X,Y and Z. Specifically, if an increase in Z is associated with a decrease in the correlation of (X,Y), then Z is a negative LA-scouting gene for (X,Y) and a negative score is assigned to quantify the strength of LA. The pair (X,Y) is called a negative LAP (liquid association pair) of Z.

Likewise, a positive LA-scouting gene can be defined. If an increase in Z is associated with an increase in the correlation of (X,Y) then the LA score is considered to be positive. Thus when comparing the low with the high expression levels of a positive LA-scouting gene, the scouted LAP is likely to change from being contra-expressed to being co-expressed. For a negative LA-scouting gene, the change goes the opposite direction from being co-expressed to being contra-expressed. In general, an LA-scouting gene serves only as a red flag, a surrogate for the intrinsic state variable that facilitates the LA activity. The protein encoded by an LA-scouting gene may not have any direct physical contact with its LAP or the proteins encoded by the genes.

For the genome wide study, there is still a computational hurdle to overcome because there are a substantial number of combinations for choosing three genes from N genes. For example, with N=5878 the number of combinations in yeast is approximately 33.8 billion triplets. It would be difficult to inspect every scatterplot in order to find all triplets with LA patterns. Liquid association is a measure that can be used to foretell if a triplet of genes is worth a closer examination. It is therefore preferable to either screen the genome to find the LA-scouting genes for a given gene required or to screen the genome to find the LAP's of a given gene.

Unlike the classic multivariate analysis, LA opens a new statistical area where marginal normality is useful but joint normality is useless. This is because if X, Y, and Z are jointly normal, then the conditional correlation between X,Y remains invariant as Z changes.

An aspect of the invention is to start from a database with many variables: standardize each variable with a normal score transformation and then compute the average product of any three transformed variable profiles to provide a database of liquid association scores.

Another aspect of the invention is to utilize the database of liquid association scores for identification of the scouting variables that mediate the correlation change of any given pair of variables.

Another aspect of the invention is to utilize the database of liquid association scores to identify liquid association pairs (LAPs) mediated by any given variable.

Still another aspect of the invention is to utilize the database of liquid association scores for identification of scouting leaders that mediate more LAPs than others.

A still further aspect of the invention is the combined use of these basic modes of utilizing the database of LA scores to generate a web of ternary scouting relationship for studying the complex systems.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Referring more specifically to the drawings, for illustrative purposes the present invention is embodied in the apparatus generally shown in FIG. 1 through FIG. 5. It will be appreciated that the apparatus may vary as to configuration and as to details of the parts, and that the method may vary as to the specific steps and sequence, without departing from the basic concepts as disclosed herein.

Figure 1:
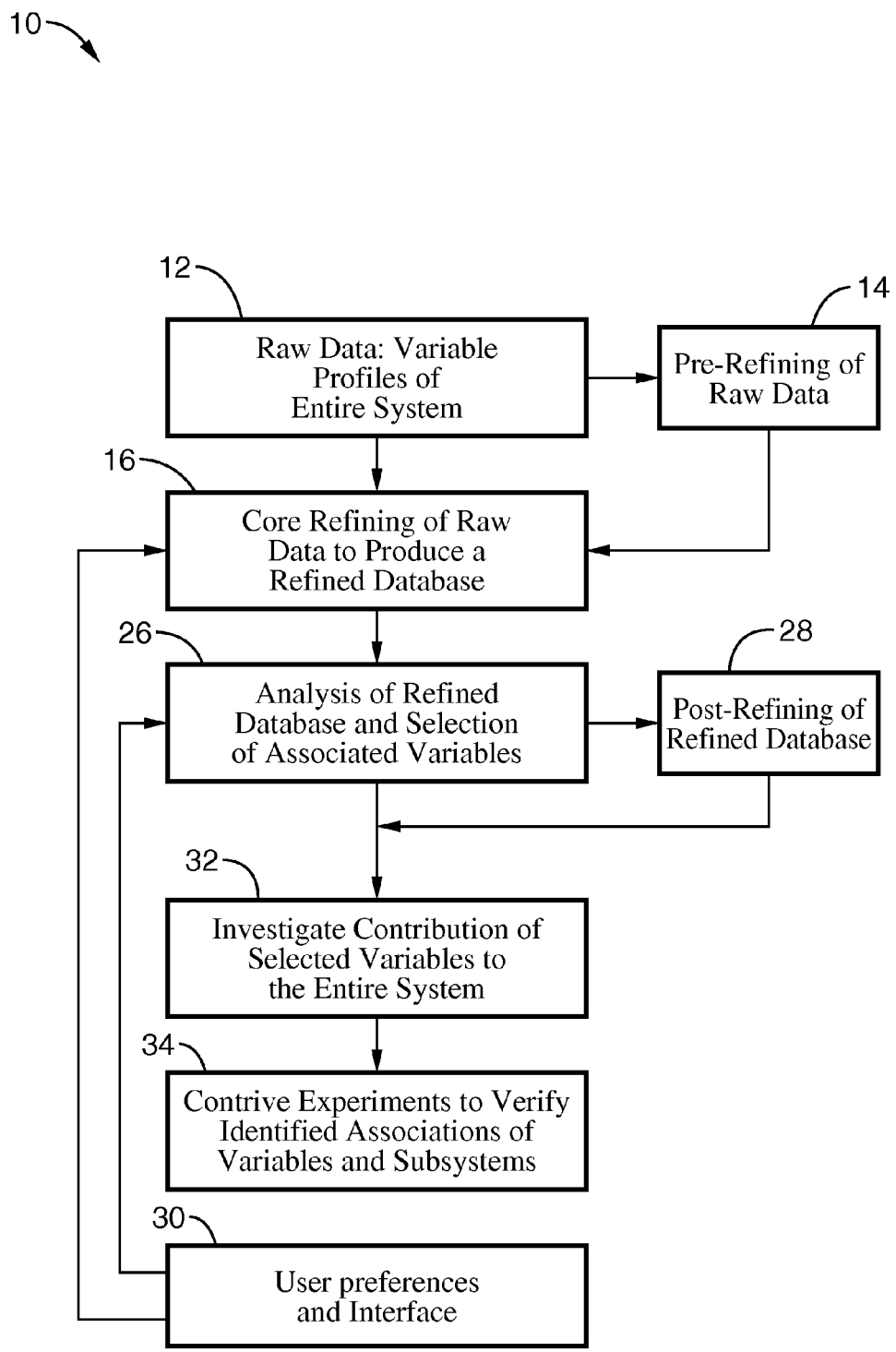
FIG. 1 is a flowchart of method steps according to one embodiment of the present invention for analyzing complex data structures.

Referring first to FIG. 1, the steps of one embodiment 10 of the method of liquid association analysis can be seen. At block 12, a database of variable profiles of preferably of the entire system is provided. Because of the broad nature of the method, liquid association has the advantage of being able to be applied to almost any large data source with complex data structures without restriction. However, the choice of database and the nature of the variables and system may limit what information can be distilled from the data. There are currently many publicly accessible databases to work with as well as large proprietary databases in the insurance, credit and stock trading industries and the like. In bioinformatics, there are many drug trial and gene expression databases of substantial volume that are publicly accessible. In addition, this invention can also be used to test the performance of any system governed by computer models where the data are often collected not empirically, but through computer simulation instead.

Often the raw data in the database comes from several different sources and is preferably standardized in terms of units and pre-refined at block 14. The raw data may be pre-refined prior to the development of the liquid association database as shown at Block 14. Errors and omissions in the raw data may lead to false positives and/or false negatives and the data may require procedures to alter or eliminate entries with missing values and the like or require the use of bootstrap, permutation and related sample reuse methods.

In addition, depending on the nature of application, global trends shared by specific or unspecific groups of variables may be removed at this stage, either because they may be deemed as artifacts or as being too obvious and thus of no interest for more advanced system analysis. Global trends can be identified by a variety of statistical methods in the art, including analysis of variance, factor analysis, principal component analysis, and various trend-removing methods in time series.

Figure 2:
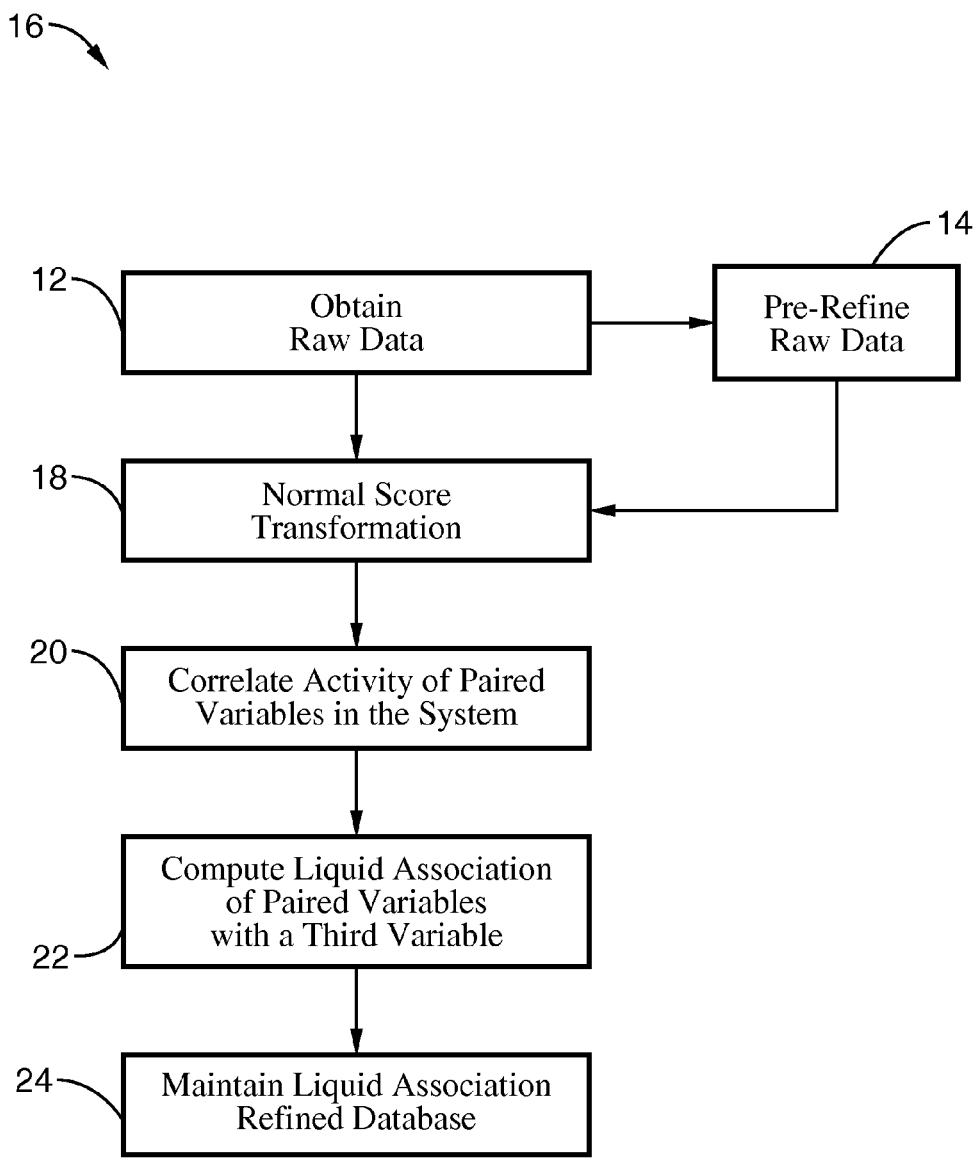
FIG. 2 is a flowchart of method steps according to one embodiment of the present invention for analyzing gene array data.

At block 16 the raw database is refined to produce a refined database called a liquid association database. Referring also to FIG. 2, the raw data is preferably refined with a three-step process that renders a refined database of liquid association for further analysis. In the preferred embodiment, the first step is to change each variable by a normal score transformation at block 18. The m values in the profile are compared with each other and their ranks $R_1, \ldots R_m$ are recorded. The ranks are then used to obtain the transformed profile, $\Phi^{-1}(R_1/(m+1)), \Phi^{-1}(R_2/(m+1)), \ldots, \Phi^{-1}(R_m/(m+1))$, where $\Phi(.)$ is the cumulative normal distribution. This produces a database of transformed normal scores.

In the normal score transformation and other refinement steps there may exist data with missing values, truncated values, and ties. In one embodiment, ties are handled by integration over the region of the ties. Another embodiment simply takes the average of the corresponding normal scores. Truncated values are treated by integration over the truncated region in another embodiment. Each variable, after normal score transformation, may not have a mean approximately equal to zero and the variance may not be one because of missing, truncation, or ties in the data. In one embodiment, the variables with too many missing values are deleted, so there is not much need to make scale adjustment.

It will also be understood that there are other ways of approximating normal distributions known in the art as well as scale adjustment that may be used. For example, certain variance-stabilizing transformations tend to normalize. The normal scores can also be computed by expected values of order statistics from the standard normal distribution.

The second step at block 20 is to correlate the activity of paired transformed variables in the system. In the preferred embodiment, the normalized values for each variable are correlated with every other variable to identify correlated pairs of variables.

In correlation-based similarity analysis, the conventional formula used is Pearson's correlation. It is well-established that this measure is most effective in depicting data pattern that has a football shape and can be approximated well by a bivariate normal distribution. The output of this step of refining will consist of N(N-1)/2 pair-wise correlations. After refining by correlation, pairs of variables that have high correlations are ready to be used for inferring functional relationships. Pairs with weak or no correlations that are traditionally ignored are the main targets of further analysis by LA method for unearthing likely causes of lack of correlation.

At block 22, the liquid association of any selected pair of variables with all of the variables is computed. The LA score is preferably computed from the average product of the three transformed profiles: $(X_1Y_1Z_1+ \ldots +X_mY_mZ_m)/m$. This step will not produce meaningful results unless the marginal distribution is known to be normal for every variable Z, which is very unlikely to be the case. This is why the first step is introduced to force the normality. Step (1) has the additional benefit that the results will be less sensitive to a few aberrantly large values.

The mathematical platform for introducing liquid association involves three random variables, X, Y, and Z, assumed to be already standardized to have mean 0 and variance 1. The correlation coefficient between X and Y is equal to E (XY). By conditioning, $E(XY)=E(E(XY|Z))=E\,g(Z)$, where $g(z)=E(XY|Z=z)$ denotes the conditional expectation of XY given Z=z. This identity simply tells us how a third random variable Z contributes to the correlation between X and Y via g (Z).

The notion of LA now arises from a straightforward dynamic perspective. We regard g(z) as the co-expression measure between gene X and gene Y when Z is at level z and ask how g(z) varies as z increases. Denote the derivative of g(z) with respect to z by g'(z). This leads to the following definition for measuring the average amount of co-expression change: Suppose X, Y, Z are random variables with mean 0 and variance 1. The liquid association (LA) of X and Y with respect to Z, denoted by LA(X,Y|Z), is LA(X,Y|Z)=Eg' (Z), where g(z)=E(XY|Z=z).

This definition can be estimated by applying one of the many existing nonparametric regression techniques to estimate the curve g'(z) first. However, given the assumption that Z follows a normal distribution and obtain the following theorem: If Z is standard normal, LA(X,Y|Z)=E(XYZ). Using Stein's Lemma, the proof is simple: Eg'(Z)=Eg(Z)Z=E (XYZ).

Stein's lemma claims that if Z is standard normal, then for any function g, the identity holds: Eg(Z)Z=Eg' (Z). Apply it with g(Z)=E(XY|Z) to get E(XYZ)=E(Z g(Z))=Eg' (Z)=LA (X,Y|Z). As proved in the theorem, if X, Y, and Z are standard normal, then LA(X,Y|Z)=LA(Y,Z|X)=L(X,Z|Y)). If X,Y, and Z are further assumed to be jointly normal, then E(X|Y, Z)=aY+b Z, E(Z|Y)=cY, E(Y|Z)=dZ, for some constants a, b, c, d, implying that $E(XYZ)=E((aY+bZ)YZ)=aE(Y^2Z)+bE(YZ^2)=acEY^3+bdEZ^3=0$. This theorem justifies why we need the normal score transformation as the first step in computing the LA score. Another advantage is that the interference of abnormally large values is tempered because only the ranks of the expression levels are used in the transformation.

Stein's lemma can also be used to derive other higher order relationships—for example, Eg" (Z)=E (XYZZ)–E(XY). Using Holder's inequality, a sharp upper bound of E(XYZ) is given by $(E|X^3|E|Y^3|E|Z^3|)^{1/3}$ is achieved under the conditions (1) |X|=|Y|=|Z| and (2) sign(X)sign(Y)=sign(Z). Similarly, a sharp lower bound of E(XYZ) is given by $-(E|X^3|E|Y^3|E|Z^3|)^{1/3}$ and this is achieved under the conditions (1) |X|=|Y|=|Z| and (2) sign(X)sign(Y)=-sign(Z). This bound may be used to standardize LA in some applications.

Generally speaking, the larger the absolute value of LA that is observed, the more significant the change in association. A positive (negative) LA indicates that g(z) tends to be increasing (decreasing respectively) in z. But technically, the LA as defined does not reflect some subtle details of the change in the whole curve g(z). For example, if g(z) behaves like $z^2$, then Eg' (Z)=0. Higher order summary like Eg" (Z), E (g' (Z))$^2$ or E|g' (Z)| can be attempted. For such generalizations, nonparametric regression may be applied to estimate g' (z) by treating XY as the output variable and Z as the input variable if the associated smoothing parameter selection problem can be satisfactorily resolved. Note also that for a triplet (X, Y, Z) with a sizable value of LA, we occasionally find that X is highly correlated with Z and Y has a quadratic trend against Z. To explain why this unusual pattern can occur, consider the degenerate case that X=Z. We can show that LA(X, Y|Z)=E YZ$^2$=E h" (Y|Z), where h(Y|Z)=E(Y|Z) by applying Stein's lemma twice. Thus in this degenerate situation, LA is estimating the curvature of the nonlinear trend between Y and Z. Lastly, due to symmetric role of X, Y, and Z in the formula E(XYZ), the measure can be interpreted either as E(X,Y|Z), or E(X,Z|Y), or E(Y,Z|X). But the detailed pattern of LA activity may not be the same for these three different cases and each pattern is preferably inspected.

Alternatively, when estimating LA, the use of Stein's lemma may not be necessary if we can directly estimate the derivative. This amounts to the smoothing problem of regressing XY against Z with focus on the derivative of the regression curve E(XY|Z). In one embodiment, an optimal smoothing parameter was chosen separately for each LA estimation. In another embodiment a common smoothing parameter was applied for all LA estimations.

Alternatively, instead of LA(X,Y|Z), a suitable higher order version can be useful for assessing the influence of the bivariate variable (Z,U) on the correlation pattern between X and Y. Algebraically, we may extend the LA method by using E(XYZU) as indices. But the question is what does it measure and when it is most effective. There are two ways to interpret E(XYZU). First, if U is standard normal, then one can prove that E(XYZU)=Eh' (U) where h(U)=E(XYZ|U). If Z and U are independent, then one can use Stein's lemma one step further to obtain that $E(XYZU)=E(g_{1,2}(Z,U))$, where $g_{1,2}(Z,U)$ denotes the second partial derivative of E(XY|Z,U)=g(Z, U).

In assessing the influence of Z on other variables, sometimes it may also be useful to consider the matrix version L(X,Y|Z), where X and Y are now random vectors, each consisting of a class of variables of interest. This yields a matrix E(XY'Z) and a singular value decomposition to reduce the dimensionality can be applied.

In other applications, it may be beneficial to consider some version of LA when Z is a categorical variable. For a binary Z (say Z taking 0 or 1 only) for example, an obvious definition is E(XY|Z=1)-E(XY|Z=0) But for the case of more than two categories, one embodiment uses the maximum from all binary differences, E(XY|Z=i)–E(XY|Z=j) where i, j are any two values that Z may take. Another embodiment considers the one-way analysis of variance by treating XY as the output and Z as group indicator. This leads to the quantity, var (E(XY|Z)).

In still other applications, such as stock market analysis, trends shared by all variables may be removed first before applying liquid association. One may also consider the following variation: (i) regress X linearly on Z to find the residual X' (ii) regress Y linearly on Z to find the residual Y' and (iii) apply L(X', Y'|Z).

In one embodiment, the use of a permutation test to tell if the LA score is statistically significant was used. The procedure generates as many as $10^5$ or $10^6$ artificial profiles Z* of Z by randomly permuting $(Z_1, \ldots, Z_m)$ and computes their LA scores. The P-value is obtained by counting how often the LA score of $(X,Y|Z^*)$ exceeds the LA score of $(X,Y|Z)$.

Figure 5:
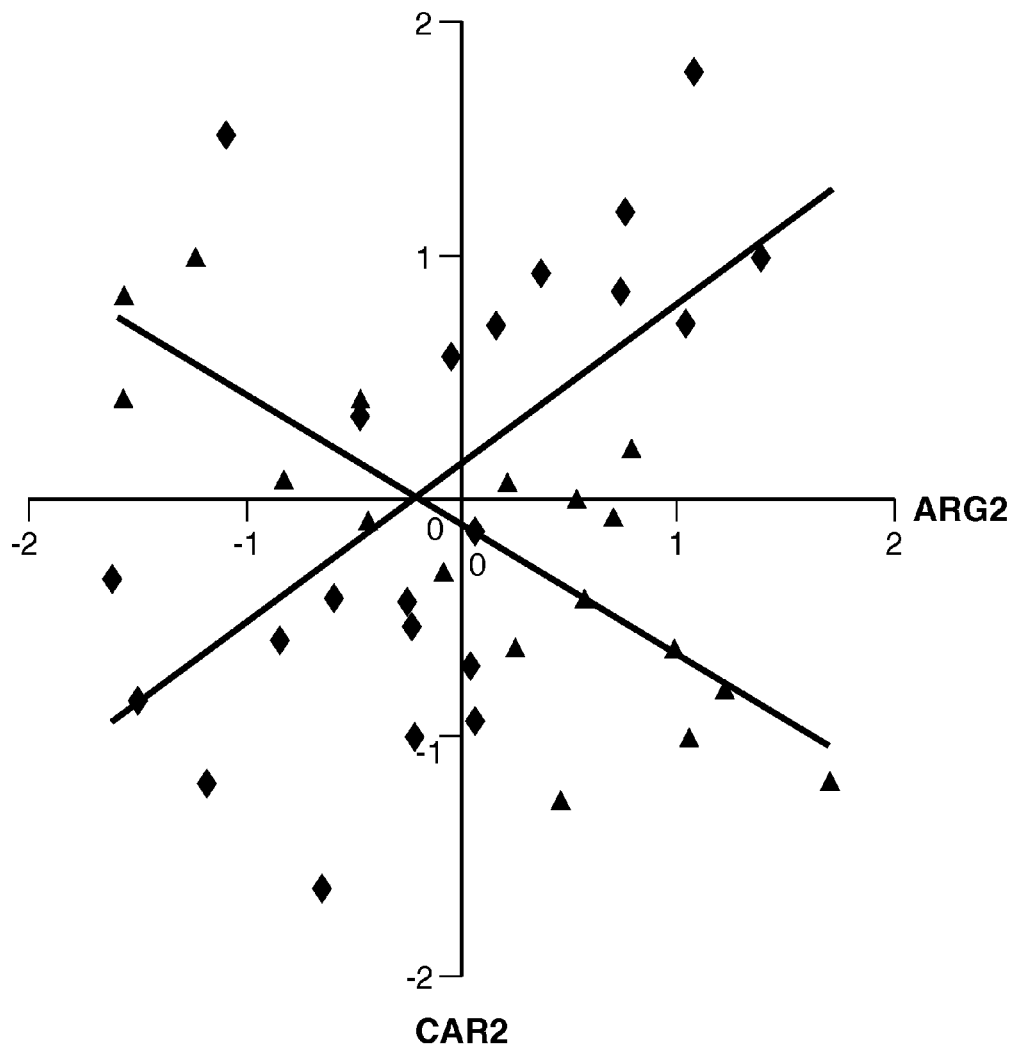
FIG. 5 is a graph of the liquid association data between ARG2 and CAR2 genes as scouted by CPA2 according to the present invention.

It can be seen that the refined liquid association based data has its own unique signature data pattern similar to FIG. 5. Note that the LA characteristic data pattern cannot be approximated by joint normal distributions even if each variable is normal. This is the theoretical reason why the information about the system behavior gathered from the products of LA-based data refinery are categorically different from those gathered by traditional similarity based methods.

While the normal score transformation enables the use of EXYZ as an effective index for identifying datasets with liquid association patterns, no index can replace the impact of graphics. For example, quadratic trends between X and Y in some high LA-scoring cases where Z is correlated with X or Y have been found. Furthermore, although this index is symmetric in X, Y, Z, the detail LA patterns for $(X,Y|Z)$, $(X,Z|Y)$ and $(Y,Z|X)$ are not always similar. Thus to take full advantage, in addition to the numerical steps for computing the LA score, the optional inspection of scatterplots for variables with high LA scores for detail LA patterns may be conducted.

It is also worthwhile to investigate other measures that may describe the LA patterns more effectively under certain situations. In one embodiment, two threshold values, $C_1 < C_2$, for Z, are found to maximize (or minimize) the difference between the sum of $X_i Y_i$ over $Z_i < C_1$ and the sum of $X_i Y_i$ over $Z_i > C_2$. This is a discrete version of the LA measure and it may work well if the change in the underlying system activity state is sharp. In one embodiment, the bivariate function XY is replaced by any other function $T(X,Y)$ to study how $E(T(X,Y)|Z) = g(Z)$ varies as Z varies. With the goal of estimating $Eg'(Z)$ in mind, Stein's lemma is applied to obtain $Eg'(Z) = E(T(X,Y)Z)$. This leads to a formula $m^{-1}(T(X_1, Y_1)Z_1 + \ldots + T(X_m, Y_m)Z_m)$ to use for substituting the default formula in data-refining. Here the profile of X consists of $X_1, \ldots X_m$ and similarly for Y and Z.

For the gene expression study, it may happen that under certain conditions, X and Y are both up-regulated and when the conditions vanish, X and Y regress to the baseline. To detect such situations more effectively, instead of considering $E(XY|Z)$, in one embodiment, threshold values $C_1$, $C_2$ are specified to declare that gene X and gene Y are both up-regulated if $X > C_1$ and $Y > C_2$. This amounts to setting the bivariate function as $T_1(X,Y) = 1$ if $X > C_1$ and $Y > C_2$ and 0 otherwise. In this embodiment, the formula reduces to a two-step procedure: find the sum of $Z_i$ over those cases where both X and Y area up-regulated, $X_i > C_1$ $Y_i > C_2$; (2) divide the sum by m. In one embodiment, $T(X,Y)$ can be set to be other indicator functions such as $T_2(X,Y) = 1$ if $X < C'_1$ and $Y < C'_2$ (both down-regulated); $T_3(X,Y) = 1$ if $X > C''_1$ and $Y < C''_2$ (one up and another down-regulated). Combinations like $T_1(X,Y) + T_2(X,Y)$ or contrasts like $T_1(X,Y) - T_2(X,Y)$ can also be used.

For the continuous case, because the theorem requires normality only for Z, the option of applying normal score transformation to Z only is provided. The original scales of X and Y may be kept or other transformations may be applied to them.

Accordingly it can be seen that the refining of the raw data produces a database of liquid association triplets at block 24 for further analysis. The database and data refining engine is preferably maintained by computer and suitable programming.

At block 26, the refined database is analyzed for liquid association pairs. In one embodiment, the absolute value $|LA(X,Y|Z)|$ is used to quantify the expressional influence gene Z exerts on or absorbs from the pair (X, Y). The pair (X,Y) is called a liquid association pair (LAP) of Z if this value is large enough. The exact cutoff point is not essential and it will be made explicit as needed. For example, a 0.35LAP means a LAP with LA greater than 0.35 and a −0.35 LAP indicates a LAP with LA smaller than −0.35. The numbers of LAPS that each variable has at various cutoff points can be shown in a LA histogram and stored as part of the database.

If an increase in Z is associated with a decrease in the correlation of (X,Y), then Z is considered a negative LA-scouting gene for (X,Y) and a negative score is assigned to quantify the strength of LA. The pair (X,Y) is called a negative LAP (liquid association pair) of Z. Likewise, a positive LA-scouting variable can be defined if an increase in Z is associated with an increase in the correlation of (X,Y), and the LA score is positive. The variables with exceptionally large numbers of LAPS (negative-LAPS, positive-LAPS) are called scouting leaders (negative-scouting leaders, positive-scouting leaders, respectively). The analysis of the database at block 26 can be directed by user preferences at block 30 so that smaller subsystems with smaller numbers of variables can be concentrated on by the investigator. Likewise, the refined liquid association database can be subject to further refinement in block 28 to reduce the number of variables for consideration to a short list of high score scouting variables Z or correlated variable pairs with a common Z variable. This list is one starting point for the investigation of the contribution that each variable makes to the entire system at block 32. It will be seen that the refined liquid association database can also be evaluated by other statistical approaches to show higher order associations in the refined database and direct the investigation of relevant variables.

The user preference and interface step at block 30 assists in the isolation of relevant triplets for further analysis from the large database. In the embodiment shown in FIG. 1, the user can narrow the scope of the raw data to be refined, the depth of the refinement as well as the scope of the analysis of the refined liquid association database.

The process of selection may be assisted by the graphic presentation of results of the data. One embodiment has a dynamic display system that allows users to visualize the interaction between a scouting variable and all variables that it mediates. In this embodiment, the display system begins with the display of scouting leaders on a computer screen. The display system branches out dynamically allowing the user to click a variable node for accessing the statistical information and linking to the outside world. In addition, all LAPs associated with the clicked variables are preferably displayed. In this way, one can see how the non-scouting leaders are associated with one or more scouting leaders. In this embodiment, the users have the option of displaying variables that are similar to (correlated with) the clicked genes. In this way, the user can review both the similarity based analysis and LA-based analysis at the same time.

In another embodiment, the computer system allows the user to model the associations that are computed from the triplet selections and any other available data pertaining to the variables. This embodiment allows the variables to be seen in context as well as the behavior of the system or subsystem as influenced by the variables.

Optionally, experiments can be contrived to verify the associations that are identified by the liquid association analysis and further study the nature of the identified variables. Resources may be devoted to identifying the function or influence of variables with previously unknown functions.

Other experiments may include the comparison of one set of results with a second set of results. For example, the liquid association methods can be used to correlate drug activity profiles with gene expression profiles. This is achieved by putting both the N gene expression profiles and the M drug activity profiles together as an enlarged system. The refined database consists of indices of LA(X,Y|Z), where X, Y, Z are any drug activity profile or gene profile. The variety of gene-drug combination offers flexibility in using the refined database that can be specified at the user preference/interface stage. For example, if X is the activity profile of a drug of interest, Y is a drug target gene profile and Z is any other gene profile, then by comparing L(X,Y|Z) over Z, the high score genes may have a role in affecting the drug activity. As an illustration, with X=MTX (Methotrexate), Y=DHFR (dihydrofolate reductase), it was found that TXN (thioredoxin) has the $4^{th}$ highest negative LA score. This signifies a central role for the thiol-disulfide redox regulation in tumor growth and drug resistance and is consistent with the view that the thioreduction system plays a role in all three major aspects with which the clinician is concerned: prevention, early detection and effective treatment.

Figure 3:
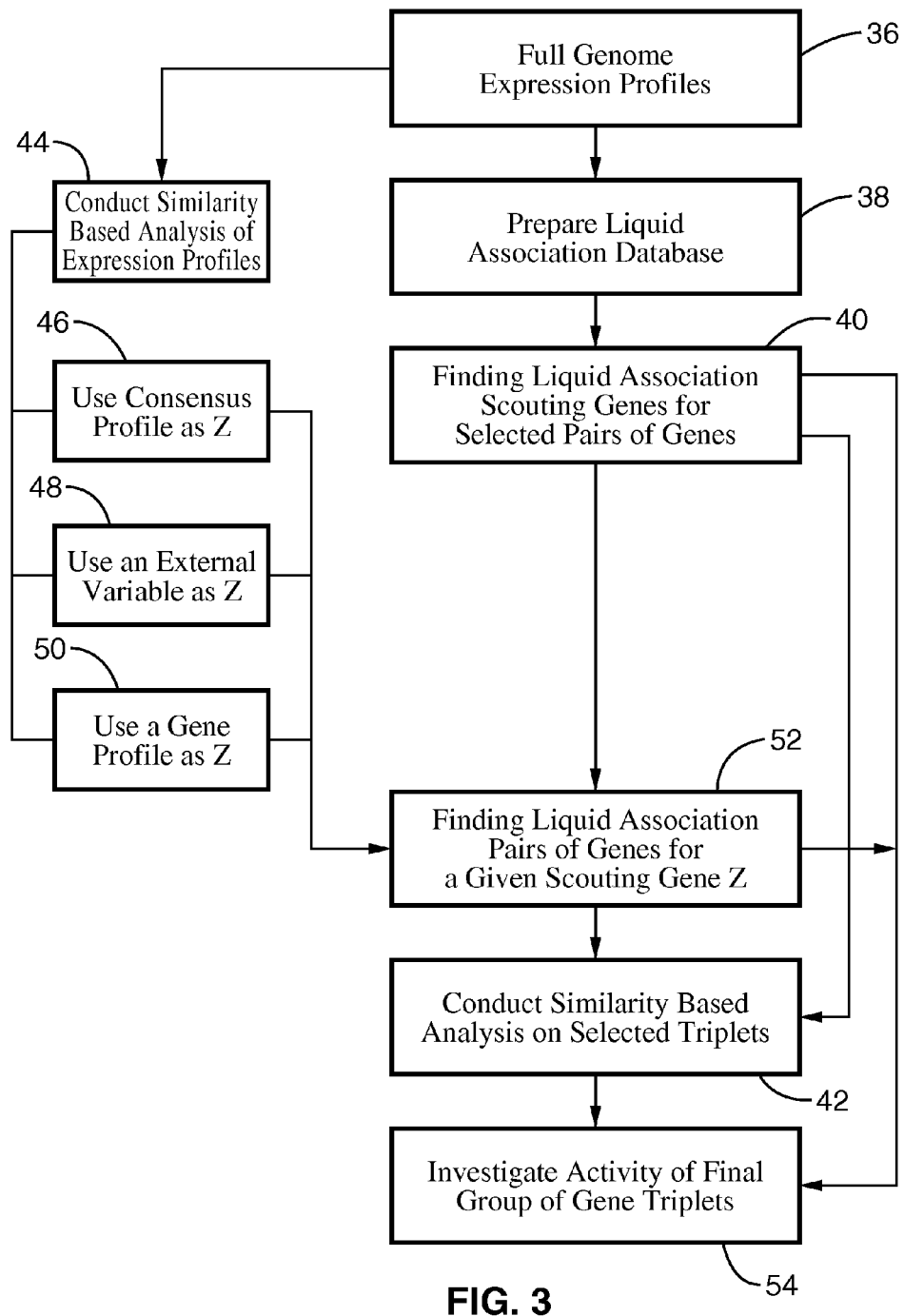
FIG. 3 is a flowchart of the substeps for the formation of a liquid association database according to one embodiment of the present invention.

Turning now to FIG. 3, an embodiment of the invention adapted for analysis of gene expression data is shown. At block 36, gene expression profiles for each gene of the entire genome are preferably provided. Modern DNA microarrays allow the simultaneous measurement of the levels of expression of thousands of genes from a single biological sample. Consequently, microarrays and genome sequencing have allowed the focus of molecular biology to the characterization of a gene or pathway on the genomic level rather than the traditional single experiment isolated on a single gene. Microarray techniques may be useful in discovering and describing genes that are involved in essential developmental, pathological and physiological processes and toxicology. Comparisons of microarray data from samples in two different biological conditions allows the detection of differential gene expression. Such comparisons allow one to determine if there is a statistically significant change in gene expression between a first condition and a second condition such as with a tumor and a normal cell or in the presence or absence of a drug.

Gene expression data may also be useful in identifying and describing regulatory networks including parallel processes that have a common control mechanism. Microarray analysis may be useful in identifying aberrant gene expression that can be used as a diagnostic indicator for certain diseases. Expression patterns can be compared between healthy and diseased cells. For example, it is beneficial to know whether a gene is switched on or off or stays on throughout all the stages of a particular disease to formulate a diagnosis or treatment.

However, inferring the underlying cellular program from the m-RNA data is extremely challenging. Unlike sequencing data, microarray measurements are "noisy." Protein abundance may not be reflected well enough by the m-RNA level because other factors like t-RNA charging, protein stability and so on are not usually considered. In addition, intrinsic variables such as the protein phosphorylation or other modification status, localization of transcription factors, quantities of important molecules like ATP, NADPH, cAMP, etc. are difficult to predict. Additionally, since mRNA is taken from numerous cells it is preferable to synchronize the phases of the life cycles of the cells.

Many similarity-based methods have proved very useful in elucidating the expression data. One procedure for observing higher level associations from microarray data is through the use of correlation. For any pair of genes (X, Y), a correlation can be computed. Then all correlations are compared with each other or with a default value to determine the statistical significance. High and significant correlation is interpreted as likely evidence for functional association between genes, meaning that their gene products are more likely to form protein complexes or participate in common metabolic or regulatory pathways and biological processes. However, these conventional methods have limitations. There are many instances where functional associations have been shown according to the literature, yet the correlation between genes is practically zero. In spite of the many successful applications reported in the literature, there is an important issue that is hard to address by profile similarity analysis. As is known, all biological processes are interlocked and many proteins have multiple cellular roles. Two proteins engaged in a common process under certain conditions, may disengage and embark on activities of their own under other conditions. This implies that both the strength and the pattern of association between two gene profiles may vary as the intrinsic cellular state changes. The aim of LA is to explore and exploit the dynamic, as opposed to the static, aspects of gene expression in cells. The method eliminates the need to specify the cellular state before applying it. Instead, the method provides results for portraying the intrinsic state that facilitates the co-expression changes. This in turn can be used to guide the specification of experiment conditions for conducting more microarray profiling.

Turning now to the step at block 38, the expression data is assembled and each gene expression profile is standardized with a normal score transformation. In general there is no reason to believe that the gene profiles are normally distributed. Therefore, it is necessary to convert the expression levels for each gene to normal scores first. After this is done, then for any triplet of genes with profiles $X_1, \ldots, X_m$, $Y_1, \ldots, Y_m$, and $Z_1, \ldots, Z_m$, the LA index amounts to a simple average of the product of the three expression profiles: $(X_1Y_1Z_1 + \ldots + X_mY_mZ_m)/m$, to produce the LA score. In one embodiment, for each gene Z, the values are summarized in a histogram. The identities of the leading 20 pairs (the number being user-specified) of genes (X, Y) contributing to each end of the histogram are also recorded.

Once the liquid association database is prepared at block 38, there are four different preferred modes of using the liquid association methods to analyze the database. At block 40 of FIG. 3, scouting genes Z are identified starting with one pair of genes (X,Y). In one embodiment, the pairs of genes (X,Y) are correlated before the Z genes are identified. In another embodiment the gene pairs are not correlated.

For this purpose, there are two types of scouting genes. A positive scouting gene mediates the change of X,Y correlation pattern from negative to positive and the score LA(X, Y|Z) is positive and a negative scouting gene mediates the change of X,Y correlation pattern from positive to negative and the score is negative. The leading LA-scouting genes can be identified from a user-specified list of candidate variables Z by comparing the LA scores LA(X,Y|Z). A formal hypothesis testing procedure can be used to check the statistical significance of a purported LA-scouting gene. A permutation test is preferred for this purpose. By default, all variables (with data available) in the system will be included in a preferably user-specified list of candidate variables. But one can restrict the analysis to a subset of special interest. For example, in a gene expression study, one may specify a functional class such as transcription factors, protein kinase, or the like. Alternatively, in gene expression-drug response study, with X being a drug profile and Y being a gene expression profile, one may restrict Z to genes only.

A similarity based analysis of the liquid association database or the selected triplets can be performed to identify correlations using conventional statistical techniques at block 42. These techniques will further reduce the number of genes in the final consideration. The resulting associations can be modeled and the specific activity of each gene in the final group can be investigated to elucidate the elements and dynamics of the system at block 54.

In another embodiment of the invention, the users can inspect the LA activity closely by studying the data plots of a few selected variables. This can be most effectively carried out via a statistical analysis package such as xlisp-stat, S plus, or R, that feature dynamic graphical analysis. For example, suppose a triplet X,Y,Z has a reasonably high LA score. If the score is computed via the default formula at the core-refining stage, then because of symmetry, it can be interpreted as either LA(X,Y|Z) or LA(X,Z|Y) or LA(Y,Z|X). Thus users should inspect all three types of LA activities.

To examine the LA activity for X,Y as mediated by Z, the user inspects the scattering pattern of the highlighted points which may be dynamically turned on and off as the browser moves up along the Z coordinate. Theoretically, for a positive LA score, one expects to find correlation changing from negative to null and eventually turning to positive. For the negative score case, the change goes just the opposite direction. The eyes can pick up more subtle features such as outliers, clusters, and the relative positions in each quadrant. Occasionally, two of the three variables may have strong correlation. If this is the case, then some quadratic trend may be observed in the other plots. In some applications, the data in a variable profile may come from several different categories. For example, the gene expression profile consists of the results from the human cancer cell lines divided into categories according to the tumor type. One can highlight the cases corresponding to one category and inspect how the distribution changes separately and compare with the behavior in other category. Such added values can be very interesting and hard to obtain by other method. The user can inspect a few LA scouting variables at the same time. Very often, correlation can be found among some of the scouting genes Z that mediate the same pair of variables (X,Y).

In another embodiment of the invention, the user begins with a given variable Z as the lead and wishes to fish out the liquid association pairs (LAPs) mediated by Z at block 52. In one embodiment, the user can specify a list A of candidate variables X and another list B of candidate variables Y. The liquid association pairs (LAPs) will be selected from any pairs (X,Y) with X from the list A and Y from the list B by comparing the LA scores LA(X,Y|Z). Again by default, A and B will include all the variables.

The scouting genes Z can be selected in preferably one of three ways. Referring now to block 44, a similarity based analysis of the genome expression data can be conducted to identify relevant genes. Clustering is arguably the most popular data-mining approach in addition to correlation. Clustering includes hierarchical clustering, Bayesian clustering, K-means clustering, Self-organization map (SOM) clustering and other known methods. A Similar analysis may be conducted at block 42.

At block 46, a consensus profile can be used to fill the role of the scouting gene profile. The consensus profile may be the simple average of a cluster of similar gene profiles identified from clustering. It can also be the principal component or eigen-gene profile of a selected set of genes participating in same pathways, sharing common motifs in the upstream regulatory regions, belonging to the same protein function classes, and the like. This is useful when the census profiles are believed to be better indicators of the shared cellular activities than other indicators.

For some applications of the methods, external variables can also be used to play the role of the scouting gene, as seen at block 48. For example, this can be the growth inhibition measure on cells under the treatment of an anticancer drug. It can also be a variable depicting the growth conditions of the cells such as the temperature or the amount of various nutrient sources.

Yet another alternative for identifying scouting gene candidates is through the use of a gene activity profile as indicated at block 50, which may be measured by different techniques, or by different experimenter groups. It can also be a protein abundance profile.

In another embodiment of the invention, the users are interested in finding the most influential variables in the system. They are allowed to specify a list of candidate variables first if needed. For each variable Z in the list, find the LAPs that are mediated by Z. Those Z variables with more LAPs than others are called the LA scouting leaders. The scouting leaders tend to play more important roles in the system than other variables.

Referring now to block 54, it can be seen that the investigation of the activity of the genes identified with the liquid association method will depend on the nature of the gene products and the subsystems that are involved and the presence of existing research in the area. One standard approach to inferring the cellular role of a protein A is to delete or over-express its encoding gene and then study how this changes the expression of other genes. Those genes with altered expression patterns are said to have genetic association with A. The way liquid association is motivated resembles this approach to an extent. The dynamic graphical exploration of the liquid association patterns for a pair of genes X, Y through varying the level of a gene Z can be viewed as one way of generating a series of "virtual" knock-out or overexpression experiments for gene Z and examining what happens to gene X and gene Y. When Z is knocked out, the expression drops to the lowest level and when Z is over-expressed, the level rising to the highest end. Although the difference from the real experiments should not be ignored (because the virtual one has no causal relationship between (X,Y) and Z) the advantage of this virtual reality approach is that every gene can be manipulated at will. The information gathered from the virtual world can help the experimental biologists in selecting a manageable subset of genes to examine more closely in the follow-up studies. In addition, the bio-system can be better understood by characterizing the difference between the virtual world and the real world through modeling.

For example, after deletion or over-expression of gene X, the experimenter decides to conduct a microarray study to see which genes have shown perturbed expression. To reduce "noise" in the microarray data while keeping the cost under control, multiple replicates of a selective subset of genes is a typical solution. But the experimenter often faces the difficult decision about what genes to include. The LAPs of X would be good candidates for consideration in focused experiments.

For more complicated experiments, a pool of equally important proteins is to be tested in vivo. However, due to budget and other practical reasons, only a small selection can be tested first. In one embodiment, a model organism that has genes producing protein sequences that are most similar to all the proteins in the pool is found as a guide. Normally the choice of this model organism is obvious. Then select a large public-accessible gene expression database for that organism and apply the LA-based data-refining. Take database of gene expression together with an additional set of genes judged as being relevant by biologists as the user-specified set in analyzing the LA database at block 30. A final list of genes whose expression are affected by genes in the database is made. The genes on the list are examined closely to determine how changing its expression level would affect the expression pattern of the model subsystem or subsystem. The gene with greater influence on the subsystem may be assigned a higher priority for testing in vivo.

Yet another example of subsequent verification is the use of a delete-lethal strain where the deletion of one or more genes leads to cell death. The study of the functions of these essential genes by the conventional genetic association approach is difficult. For some of these essential genes, occasionally, biologists find out that cells may survive if another gene is deleted or overexpressed at the same time. This typically requires a lot of experimentation. Thus this is an ideal case for using the virtual reality approach. One can start with an essential gene and find a subsystem affected by the gene. Genes in this subsystem will be the candidates for conducting the knockout/over-expression experiments.

Microarrays are often used for finding the differential gene expression patterns between tumor and normal cells, cells of different tumor types, or cells from different sex, age group, or other phenotype of clinical relevance. Comparison study is also important in developing tumor specific drugs.

In cancer therapy development, ideal drug or drug combinations to treat a tumor must be selected according to the phenotypic characteristics of the cancer cells. Comparative experiments can be analyzed at three levels. The first level is to compare the average expression level of a gene. Genes showing greatest differences (relative to the noises) are identified. The second level is to compare the co-expression patterns using similarity based analysis. The third level is to compare the co-expression dynamics using the LA-based analysis. The third level analysis can detect if inherent flow of an important metabolic pathway is coherent or not. Predictably many diseases can be caused by metabolite accumulation, and the identification of key regulatory genes (playing roles similar to SCH9 in regulating urea cycle expression pattern in example 1) is important. Such genes, which are hard to detect at the first or second level of analysis, can be examined further in the follow-up studies, to see if any mutation has occurred in the coding and non-coding regions, or to find if there are other factors such as the cellular localization, protein modification, transcription factors and so on, that may regulate the expression of these genes. The LA-based method can also be applied to signal transduction or other gene expression pathways.

The present invention may be more particularly described in the following examples that are intended for illustrative purposes only, since numerous modifications, adaptations and variations will be apparent to those skilled in the art.

EXAMPLE 1A

Yeast, *Saccharomyces cerevisiae*, is a genome that has been fully sequenced and has microarray data publicly available and is used as a model as one illustration of the methods. The data used comes from four cell-cycle experiments, which are accessible online. All of the data was used to construct gene profiles with a total of 73 conditions. Genes with too many missing values are excluded, leaving a total of 5787 genes under study. After ranking all possible pairs (over 17 million pairs in total) by their LA-scores, only the top 20 positive LAP's and top 20 negative LAP's of each gene were collected for further use in examples 1B through 1F.

Figure 4:
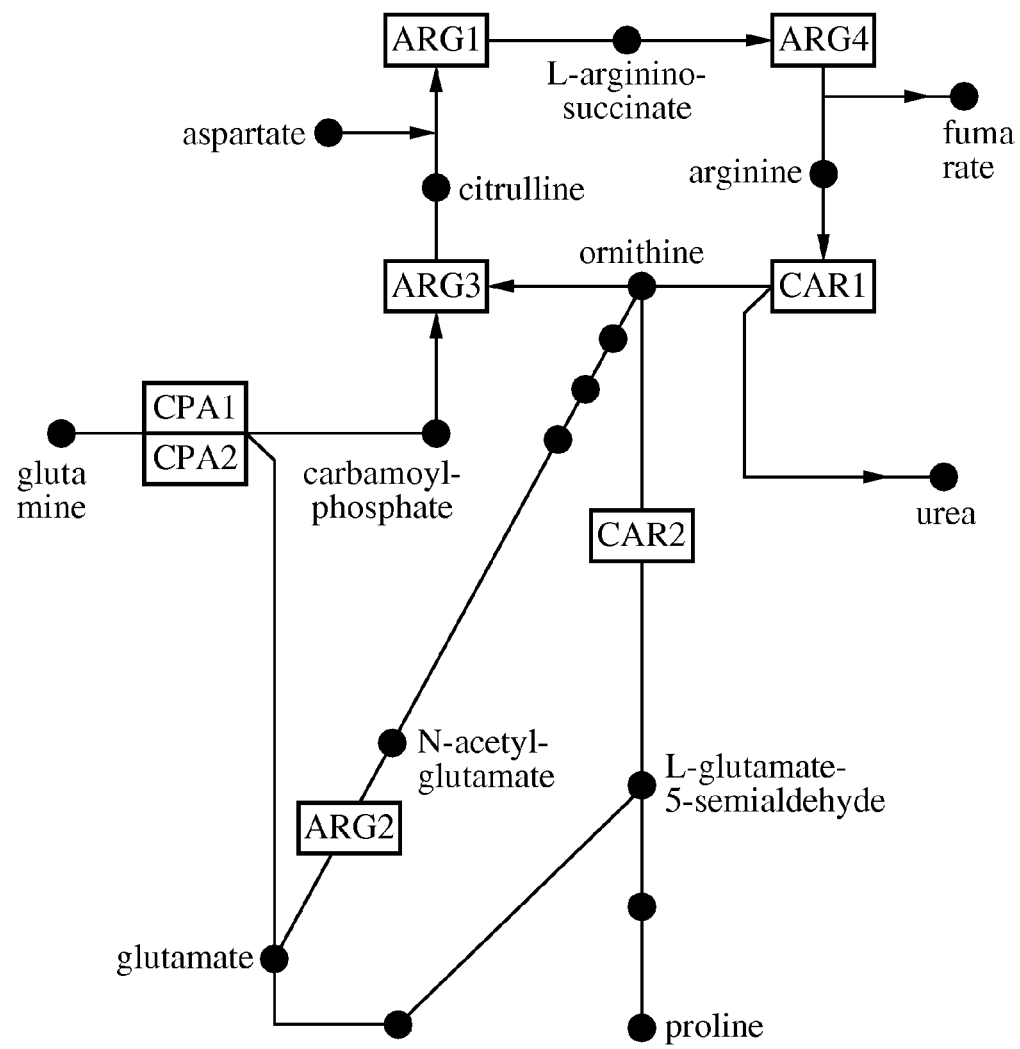
FIG. 4 is a schematic representation of the Urea cycle/arginine biosynthesis pathway including the names of relevant genes.

Referring now to FIG. 4, a schematic of the urea cycle with key enzymes and intermediates is shown. First, consideration is paid to two functionally associated genes, GLN3 and CAR1. CAR1 encodes arginase, the enzyme catalyzing the hydrolysis of arginine into urea, while GLN3p is a transcription factor known to activate nitrogen-catabolic genes including CAR1. While a positive correlation between the two profiles is expected, very little similarity in fact exists between the two expression profiles.

To apply the Liquid Association methodology, (GLN3, CAR1) was taken as the pair (X, Y), and any gene is selected as Z, and the LA-score as defined earlier were computed. All 5878 genes were then ranked as a positive or negative LA-scouting gene by ordering their LA-scores. It was found that at the $8^{th}$ place leading negative score was ARG4, the gene immediately ahead of CAR1 in the urea cycle. It was also seen that ARG4 and its two proceeding genes in the FIG. 4 flow chart, ARG1, ARG3, share some mild degree of profile similarity. However, these three genes are not co-expressed with ARG2, the gene encoding acetylglutamate synthase which carries out the first step in synthesizing ornithine and eventually arginine. This may be due in part to the presence of CAR2p (ornithine aminotransferase). In order to feed ornithine into the arginine biosynthesis pathway, CAR2 should be inactivated to avoid the immediate degradation of ornithine. This suggests that CAR2 and ARG2 may be contra-expressed. However, this suggestion is not supported by the traditional Pearson profile data since the correlation between ARG2 and CAR2 is nearly zero.

Referring also to FIG. 5, the Liquid association between ARG2 and CAR2 as scouted by CPA2 is shown. Using the Liquid Association method on the data, the genes (ARG2, CAR2) were treated as the gene pair (X,Y). Again all the genes were ranked by their LA-scouting abilities for this pair. Among the leading 10 negative LA-scouting genes for (ARG2, CAR2), was found the gene CPA2, which encodes the large subunit of carbamoylphosphate synthetase. Note that carbamoylphosphate is needed for ARG3p to synthesize citrulline from ornithine. Thus high expression of CPA2 may reflect the state of cellular demand for arginine.

From the graph shown in FIG. 5 is can be seen that when the expression level of CPA2 is low, as represented by the diamond shapes, a positive correlation is seen between ARG2 and CAR2. As the level of CPA2 increases, the correlation pattern is gradually weakened. Eventually, when CPA2 is high, shown as triangles, the association has turned into a negative. The LA score is −0.289. For efficient activation of the arginine biosynthesis pathway, up-regulation of ARG2 must be concomitant with down-regulation of CAR2 to prevent ornithine from leaking out of the urea cycle. We see this occurs only when CPA2 is up-regulated. Because activation of CPA2 provides the influx of carbamoyl phosphate into urea cycle, high expression level of CPA2 can be interpreted as a physiological signal for arginine demand. When the demand is relieved and CPA2 is lowered, CAR2 is up-regulated, opening up the channel for orinthine to leave the urea cycle.

Therefore, from the LA-activity, it can be seen that under this state, ARG2 and CAR2 are indeed negatively correlated. A similar interpretation can be given to the LA activity between (GLN3, CAR1) with ARG4 being the scouting gene. Because ARG4p catalyzes the last step of arginine biosynthesis, high expression of ARG4 can be viewed as a cellular signal for arginine demand as well. Thus if CAR1 were also up-regulated, then the newly synthesized arginine would be subject to immediate hydrolysis by CAR1p, leading to a wasteful cycle of metabolism. Such nutrient-wasteful species would be less likely to survive during the course of evolution.

Likewise, the up-regulation of GLN3 is also concomitant with higher expression of CAR1 when ARG4 is expressed at the low level. Overall, the LA scores are statistically significant. For (GLN3, CAR1|ARG4), the score is −0.2589 with the P-value 74 out of 100,000. For (CAR2, ARG2|CPA2), the score is −0.2894 with the P-value 56 out of a million.

EXAMPLE 1B

The yeast gene SCH9 has been shown to have a role in aging and it is suggested that common processes control the life-span of most organisms, including worms, flies, and possibly mammals. SCH9 encodes a serine/theorine protein kinase. It is required for the nitrogen activation of the fermentable-growth-median-induced pathway. Ideally, the entire urea cycle genes should be coherently expressed in such a way that not only positive correlation exists among ARG1, ARG2, ARG3, ARG4, but concomitantly, these genes should also be negatively correlated with CAR1. This turns out to be the case when the expression of SCH9 is low.

Examining the 40 LAPs of SCH9 that were derived, the pair (ARG1, ARG2) that are involved in the arginine biosynthesis pathway was found as a negative LAP of SCH9. It was found that the expressional pattern between ARG1 and ARG2 evolves as SCH9 varies. At low levels of SCH9 activity, ARG1 and ARG2 are positively correlated. This indicates that the coordination of expression between these two regulators of the arginine synthesis pathway improves when the cellular need for SCH9 is lowered.

Furthermore, since the SCH9-deletion mutants have been shown to have a longer non-dividing life span than the wild type, there is a likely association between the efficient usage of urea cycle and the longevity physiology. Two mutants that have been isolated and the affected genes were SCH9 and CYR1 (encoding adenylate cyclase). The longevity regulation by SCH9 and CYR1 is consistent with an oxidative-damage theory of aging.

When identifying the LAP's of CYR1, an oxidative protection gene TTR1/GRX2 (glutaredoxin), two age-related genes SIM1 and HST3 were found. HST3 is a homolog of the gene SIR2 that encodes NAD-dependent histone deacetylase and regulates the replicative lifespan of yeast. Interestingly, ARG4 was found to be one LAP of SIR2.

From the LAPs of CYR 1, there are five genes involved in glutamate metabolism and nitrogen utilization: PUT2, LYS9, ARO9, GAP1, and MEP2. Glutamate, a product of most amino acid deamination, is at the head of the ornithine/arginine biosynthesis/urea cycle pathway. Standard profile similarity analysis indicates that SCH9 is positively correlated with CAR2. Thus lowering the SCH9 expression is concomitant with the down-regulation of CAR2, thereby preventing the leakage of ornithine from the urea-cycle.

EXAMPLE 1C

Glycolysis is perhaps the most completely understood metabolic pathway in yeast. It involves 10 enzymatic reactions by which glucose is converted to pyruvate with the generation of 2 mol of ATP (adenosine triphosphate) per mol of glucose. Gluconeogenesis, the biosynthesis of glucose from noncarbohydrate precursors, works in the opposite direction. A total of 35 yeast genes related to either pathway are listed under the energy category according to MIPS.

Of the computed LAP's for the glycolytic pathway genes, there were two genes, PFK1 and PFK2 that stand out from the rest of the group. These genes encode the alpha and the beta subunits of 6-phosphofructokinase (Pfk) respectively. The profound impact of PFK1 and PFK2 at the expression level reflects the critical role that their proteins play in the system. Pfk is the major flux-controlling enzyme of glycolysis in muscle and is the principal rate-limiting enzyme of the entire pathway of glycolysis.

In humans, deficiency of Pfk can cause glycogen storage disease and muscle cramps. The 3-D structure of Pfk shows a heterooctamer of four alpha and four beta chains. It catalyzes the third reaction of glycolysis by phosphorylating fructose-6-phosphate (F6P) to yield fructose-1,6-diphosphaste. As mounting evidence has revealed, how Pfk exerts control over glycolysic and other pathways is delicately mediated by important metabolic substances including ATP, AMP, pruvate, and Acetyle-CoA.

EXAMPLE 1D

Mitochondria generate energy through the process of oxidative phosphorylation. During the process, electrons are passed along a series of respiratory enzyme complexes located in the inner mitochondrial membrane, using the released energy to pump protons across the membrane. The proton gradient then enables the making of ATP by ATP synthase ($F_1F_0$ ATPase, or Complex V). Many of the encoding genes in the pathway have been shown to be co-expressed. One interesting example is cytochrome c1 that acts as the last leg for the complex III (cytochrome $bc_1$) in relaying electrons to cytochrome c. In the case of S. Cerevisiae, cytochrome c1 is encoded by a single gene CYT1. From the profile similarity analysis, the gene QCR8 (ubiquinol cytochrome reductase subunit 8), from complex III, and two genes COX5a and COX8, from complex IV (cytochrome oxidase) were found to be among the top 20 genes with expression profiles most similar to CYT1. Complementing this finding, the LA method links CYT1 to genes further down the electron transport pathway. From the 40 most significant LAPs of CYT1, it was found that two of them, ATP1 and ATPS, encode subunits from the mitochondrial ATP synthase. In fact, ATP1 ($F_1$ alpha subunit) appears in the group 11 times.

EXAMPLE 1E

Calmodulin is a ubiquitous $Ca^+$ binding protein that regulates a wide range of proteins and processes in all eukaryotes. It is encoded by CMD1 in S. cerevisiae. The best-known binding target of calmodulin in mitosis is Nuf1 p. Nuf1p is a component of spindle pole body, the yeast microtubule organizing center wherein calmodulin is localized. Despite of the functional association between their gene products, CMD1 and NUF1 do not have similar expression profiles. NUF1 does not appear in the 40 LAPs of CMD1 either. Instead, it is found to be paired with an unknown gene YGL149W as a positive LAP of CMK1, one of the two genes encoding the calmodulin-regulated protein kinase. More interestingly, YGL149W also appears in one of the 20 positive LAPs of CMD1. Indeed, although the profiles of CMD1 and CMK1 are not similar, they do share 9 genes in their LAPs. Furthermore, YGL149W has the protein-protein interaction with CRM1p (beta karyopherin, involved in exporting certain proteins from nucleus) that in turn interacts with NUF1p. Consistent with this connection, it was seen that KAP120 (a member of karyopherin family) is in the group of LAPs of CMD1 and SXM1 (putative beta karyopherin) and in the group of LAP's of CMK1. From the joint LAP lists for CMD1 and CMK1, a convergence of a number of genes involved in the signal transduction pathways for various types of growth morphogenesis such as sporulation, pheromone response, pseudohyphal growth, RAS, MAPK (mitogen activated protein kinase), cAMP-PKA, and HOG (high osmolarity glycerol response) pathways: IME1, RIM13, SSP1, SOK2, MUC1, TEC1, PTP3, PTC1, SIP4, CDA2, IME4, KAR4, KAR2, DOC1, AXL1, OPY1, ERF2 can be seen.

EXAMPLE 1F

Genes with an exceptionally large number of either negative or positive Liquid Association Pairs, are considered scouting leaders and grouped together. LA Scouting leaders may also be negative or positive. The LA-scouting leaders are often found to scout each other. For example, among the top 10 LA-negative and 10 LA-positive scouting genes for (CYR1, PFK1), 7 are LA-scouting leaders.

Using stringent selection criteria discussed above, a set of 66 genes with highest LA-scouting ability was selected. Some of the selected LA-scouting leaders are well-studied genes including, for instance, CYR1, PFK1, TPS/(trehalose-6-phosphate synthase), TPS2(trehalose-6-phosphate phosphatase), GSY1 (glycogen synthase isoform 1), GLC3 (Alpha-1,4-glucan branching enzyme), ATP1, PPA1 (subunit of vacuolar ATPase), QCR9 (ubiquinol cytochrome c reductase subunit 9), CYC7(cytochrome c, isoform 2), ERG13(3-hydroxy-3methylglutaryl coenzyme A synthase), AAT2 (aspartate aminotransferase), APC1 (largest subunit of anaphase promoting complex), IME1 (positive regulator of sporulation genes).

The selection of LA-scouting leaders is by no means definitive and is intended to be flexible. GSY2 (dominant isoform of glycogen synthase) just misses the cut. PFK2 and YAP6 would have been included if not for the missing data in one of the four cell-cycle experiments. YAP6 encodes a transcription factor homologous to YAP1p (basic leucine zipper, yeast homolog of c-Jun). Over-expression of YAP6 increases resistance to cisplatin, one of the most widely used drugs for cancer chemotherapy. These genes may be considered LA-scouting leaders in other settings.

The Liquid Association system creates a portrait of the cellular context in which a gene is likely to be involved. This is useful for predicting the functions of little-known genes. For example, one vaguely understood LA-scouting leader is the gene ECM1. The literature on ECM1 is quite thin and its functional annotation is still vaguely put as "involved in cell wall biosynthesis" by MIPS.

Among the scouting targets of ECM1, are several genes that are involved in translation. For example, gene NIP7 (required for efficient 60S ribosome subunits biogenesis, delete-lethal), appears six times. This is consistent with the recent finding that ECM1p tagged with GFP is localized in the nucleus with a mild enrichment in the nucleolus and that ECM1p genetically interacts with MTR2p in the 60S ribosomal protein subunit export. Coincidentally, NIP7p appears as one of the 23 proteins co-purified with NUG1p. The chance for this coincidence to occur by a fluke is less than 0.5%. This re-assures the biological relevance of the LA approach in protein function prediction.

The gene YNL101W is another LA-scouting leader, which is still considered as an unknown gene in SGD and MIPS at the present time. From the list of LAPs for YNL101W, there are several genes involved in autophagy, protein degradation and transport: AUT7 (essential for autophagy; appearing six times); PRE6 and PUP1 (20S proteasome subunits); RPT6 (26S proteasome regulatory subunit); CLC1 (clathrin light chain); YPT52 (GTP binding protein of the RAB family); UBP2 (ubiquitin specific protease). This appears consistent with the newly identified role of YNL101W (newly named AVT4) as a membrane transporter responsible for the efflux of tyrosine and other large neutral amino acids from vacuoles.

Accordingly, it can be seen that the diversity of functions of the known LA scouting genes makes the LA scouting gene grouping an ideal list of genes as landmarks for surveying the full genome expression network.

EXAMPLE 2

There are numerous factors that can contribute to drug sensitivity. Extensive studies have been conducted on issues such as drug transport, modification, translation regulation of the target gene, cell cycle arrest, and programmed death. But the drug resistance problem is complex and we ask if there is any general computational method for augmenting the sketchy results established by biochemical approaches. For most cases, there is essentially no statistical correlation between the drug activity profile and the expression profile of the drug's known molecular target or its known drug resistance gene. This is the ideal situation for applying the Liquid Association method.

The use of Antifolate compounds in chemotherapy has a long history in medicine. Temporary remissions in acute leukemia in children produced by folic acid antogonist, 4-aminopterolyl-glutamic acid (aminopterin) have been seen. For example, Methotrexate (MTX) is an antifolate that has been used for treatment of non-Hodgkin's lymphoma, osteogenic sarcoma, chorocarcinoma and carcinomas of breast, head and neck. The molecular target of MTX is DHFR (dihydrofolate reductase). MTX and its polyglutamated forms are tight binding inhibitors of DHFR. The inhibition results in the quick conversion of all of a cell's limited supply of THF to DHF by the thymidylate synthase (TYMS) reaction. This prevents dTMP synthesis and also blocks other THF-dependent reactions of purine, histidine and methionine biosynthesis. The correlation between MTX and DHFR and that between MTX and TYMS are weak.

From the short list of the significant LA-scouting genes for (MTX, DHFR) and that for (MTX, TYMS), two genes TXN (thioredoxin) and TXNRD1 (thioredoxin reductase) are found. This signifies a central role for the thiol-disulfide redox regulation in tumor growth and drug resistance. In fact, thioredoxin reductase is itself a patheophysiological factor and drug target.

Other LA-scouting leaders from the gene expression data includes metastasis suppressors TIMP2, TIMP3, TIMP1 (tissue inhibitor of metalloproteinase), MMP-14(membrane-type matrix metalloproteinase 1; forming a trimolecular complex with pro-MMP-2 and TIMP-2), HPT-1 (CDH17, LI-cadherin; a marker of gasteric metaplasia and neoplasia, (35)) and genes involved in signal transduction and cell growth like EPHA2 (epithelial cell receptor protein tyrosine kinase; regulated by p53 tumor suppressor protein and inducing apoptosis, (36)), EPS8 (epidermal growth factor receptor pathway substrate 8), SGK (serum/glucocorticoid regulated kinase), CDK6(cyclin-dependent kinase 6); LGLS3(Galectin 3, lactose-binding lectin involved in cell growth regulation).

Several other genes of great importance in oncology are also found to play interesting roles as LA-Scouting genes, including P53 and BCL-2. There are many other genes of unknown functions that also appear in the short list of LA-scouting genes that are of great interest to direct the future research drug developers and investigators.

EXAMPLE 3

The development of cancer or other genetic diseases is likely to be coupled with the incoherent expression between important genes in the diseased cells. In contrast to most comparative gene expression studies, which mainly focus on the identification of differentially expressed genes between the normal sample and the tumor sample, an investigation of the changes in the second or higher order gene profiles can be conducted with the Liquid Association method. As an illustration, colon carcinoma expression data was used which has 40 tumor and 22 normal tissue samples. After pre-processing the data for chip-to-chip adjustment and normal score transformation, for any two genes X and Y, the computation $E(XY|Z=1)-E(XY|Z=0)$ was used, where $Z=1$ indicates a normal sample and $Z=0$ indicates a tumor sample. Gene pairs exhibiting large disparity in covariance were obtained.

Upon review of the LA data, one LA pair of genes with the most negative value was MXI1 and an mRNA, M63964, encoding nucleoside diphosphate kinase (NDPK). Since NDPK is highly conserved, the expression may be due to cross-hybidization of homologous genes. Indeed, there is a highly homologous human gene NME1 (nm23-H1) in the dataset that correlates with M63964 very well. NME1 is the first identified metastasis-suppressor gene.

Transfection of nm23-H1 cDNA into highly metastatic murine melanoma, rat mammary adenocarcinoma, and human breast cancer and melanoma cells has been shown to reduce their invasiveness and metastatic ability in vivo. However, for human colon tumors, it has been reported that the mRNA levels increased rather than decreased as expected in 33 out of 41 colon tumors relative to that in matched normal mucosa. NME1 encodes the subunit A of NDPK. The current sentiment is that the clinical relevance of nm23-H1 as metastasis suppressor remains enigmatic because its expression appears to be tissue-dependent. Even more puzzling is the fact that the unit B of NDPK encoded by NME2, which is also homologous to M63964, can bind and activate the oncogene c-MYC. Accordingly, it is suggested that there may be unknown alternative mechanisms that inhibit the effects of NME1. The Liquid Association results support this suggestion. The results suggest that MXI1 expression may be involved in the inhibitory process for the following reasons. First, MXI1 is a transcription factor, known to be a Myc antagonist. Its tumor suppressing capability comes from the competitive binding with a heterodimerization partner protein, MAX, of c-Myc. In addition, low expression of NME1 and NME2 decreases the c-MYC binding activity, making the tumor-suppressing task of MXI1 easier to accomplish. Note that c-MYC is highly expressed in more than 70% of human colon cancers.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for identifying patterns of gene expression within a cell of an organism, comprising:
   sequencing the genome of a cell to identify genes;
   measuring the expression of said genes over time;
   correlating the activity of each gene with the activity of every other gene in the genome to produce pairs of correlated genes;
   associating the activity of each gene with the correlated activity of said pairs of correlated genes;
   identifying scouting genes from the associated activity of each gene with the activity of said pairs of correlated genes; and
   evaluating the biological characteristics of the products of said scouting genes and said pairs of correlated genes.

2. A method as recited in claim 1, further comprising:
   identifying the association of a first scouting gene with a second scouting gene to identify patterns of gene expression and suppression in an organism.

3. A method as recited in claim 1, wherein said measuring step comprises:
   measuring a quantity of mRNA for each gene over time as a measure of gene expression.

4. A method as recited in claim 1, further comprising:
   investigating a biological activity of said identified scouting genes in a cell.

5. A method as recited in claim 1, further comprising:
   modeling biological activity of said identified genes in the organism.

6. A method for identifying patterns of irregular gene expression in tumor cells, comprising:
   measuring gene expression for a plurality of genes in a normal cell;
   correlating the activity of each gene with the activity of every other gene of said plurality of genes to produce pairs of correlated genes;
   associating the activity of each gene with the correlated activity of said pairs of correlated genes to form a baseline pattern of normal gene activity;
   measuring gene expression for a plurality of genes in a tumor cell;
   correlating the activity of each gene with the activity of every other gene of said plurality of genes to produce pairs of correlated tumor cell genes;
   associating the activity of each gene with the correlated activity of said pairs of correlated tumor genes to form a baseline pattern of tumor gene activity; and
   comparing the baseline pattern of normal gene activity with the baseline pattern of tumor gene activity to determine differences in the activity patterns.

7. A method as recited in claim 6, further comprising:
   evaluating the biological properties of the gene products of the genes that are expressed differently in the tumor cell than in the normal cell.

8. A method as recited in claim 6, wherein said associating step of said normal cell measurements further comprises:
   identifying scouting expression genes from the associated activity of each gene with the activity of said pairs of correlated genes; and
   evaluating the biological characteristics of the products of said scouting genes and said pairs of correlated genes.

* * * * *